US010311316B2

(12) United States Patent
Matthews et al.

(10) Patent No.: US 10,311,316 B2
(45) Date of Patent: Jun. 4, 2019

(54) APPARATUS, METHOD AND COMPUTER PROGRAM FOR IDENTIFYING BIOMETRIC FEATURES

(71) Applicant: Nokia Technologies Oy, Espoo (FI)

(72) Inventors: Andrew Matthews, Cambridge (GB); Christopher Bower, Cambridge (GB); Troels Ronnow, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/526,929

(22) PCT Filed: Nov. 11, 2015

(86) PCT No.: PCT/FI2015/050782
§ 371 (c)(1),
(2) Date: May 15, 2017

(87) PCT Pub. No.: WO2016/079378
PCT Pub. Date: May 26, 2016

(65) Prior Publication Data
US 2017/0323172 A1 Nov. 9, 2017

(30) Foreign Application Priority Data
Nov. 21, 2014 (EP) .................................... 14194387

(51) Int. Cl.
G06K 9/74 (2006.01)
G06K 9/20 (2006.01)
(Continued)

(52) U.S. Cl.
CPC .......... G06K 9/2027 (2013.01); A61B 5/0035 (2013.01); A61B 5/0037 (2013.01);
(Continued)

(58) Field of Classification Search
CPC .................................................... G06K 9/2027
(Continued)

(56) References Cited

U.S. PATENT DOCUMENTS 5,541,994 A * 7/1996 Tomko ............... G06K 9/00006
380/285
7,225,005 B2 * 5/2007 Kaufman ........... A61B 5/14535
600/310
(Continued)

FOREIGN PATENT DOCUMENTS

EP 1025677 8/2000
EP 2413263 A1 2/2012
(Continued)

OTHER PUBLICATIONS

Office action received for corresponding Vietnamese Patent Application No. 1-2017-02130, dated Jul. 19, 2017, 1 page of office action and 1 page of translation available.
(Continued)

Primary Examiner — Roy M Punnoose
(74) Attorney, Agent, or Firm — Harrington & Smith

(57) ABSTRACT

A method, apparatus and computer program, wherein the method comprises: illuminating a portion of skin of a user; detecting light scattered by the illuminated portion of skin and using the detected light to identify locations of biometric features within the illuminated portion of skin; and configuring a light source to selectively illuminate identified locations of biometric features.

18 Claims, 10 Drawing Sheets

(51) Int. Cl.
  *A61B 5/024* (2006.01)
  *G06K 9/00* (2006.01)
  *A61B 5/1171* (2016.01)
  *A61B 5/00* (2006.01)

(52) U.S. Cl.
  CPC ............ *A61B 5/024* (2013.01); *A61B 5/1171* (2016.02); *A61B 5/489* (2013.01); *G06K 9/00885* (2013.01); *G06K 2009/00932* (2013.01); *G06K 2009/00939* (2013.01); *G06K 2009/00953* (2013.01)

(58) Field of Classification Search
  USPC .......................................................... 356/71
  See application file for complete search history.

(56) References Cited

U.S. PATENT DOCUMENTS

| | | | |
|---|---|---|---|
| 2006/0129037 A1* | 6/2006 | Kaufman | A61B 5/14535 600/322 |
| 2006/0129038 A1* | 6/2006 | Zelenchuk | A61B 5/14535 600/322 |
| 2007/0253602 A1 | 11/2007 | Amano | |
| 2008/0068591 A1* | 3/2008 | Kono | G06K 9/00 356/71 |
| 2008/0186260 A1 | 8/2008 | Lee | |
| 2008/0188726 A1 | 8/2008 | Presura et al. | |
| 2009/0060301 A1 | 3/2009 | Carver et al. | |
| 2009/0226071 A1 | 9/2009 | Schuler et al. | |
| 2010/0049017 A1 | 2/2010 | LeBoeuf et al. | |
| 2010/0065834 A1 | 3/2010 | Hammond | |
| 2012/0150387 A1 | 6/2012 | Watson et al. | |
| 2012/0271121 A1 | 10/2012 | Della Torre et al. | |
| 2013/0197319 A1 | 8/2013 | Monty et al. | |
| 2013/0331663 A1 | 12/2013 | Albert et al. | |
| 2014/0070191 A1 | 3/2014 | So et al. | |
| 2014/0089672 A1 | 3/2014 | Luna et al. | |
| 2014/0107493 A1 | 4/2014 | Yuen et al. | |
| 2014/0107495 A1 | 4/2014 | Marinelli et al. | |
| 2014/0107498 A1 | 4/2014 | Bower et al. | |
| 2014/0135631 A1 | 5/2014 | Brumback et al. | |
| 2014/0196131 A1 | 7/2014 | Lee | |
| 2014/0246917 A1 | 9/2014 | Proud et al. | |
| 2016/0290926 A1* | 10/2016 | Notingher | G01N 33/4833 |

FOREIGN PATENT DOCUMENTS

| | | |
|---|---|---|
| JP | 2013-212315 A | 10/2013 |
| KR | 100880392 B1 | 1/2009 |
| WO | 0169520 | 9/2001 |
| WO | 2005/104075 A2 | 11/2005 |
| WO | 2013/017605 A1 | 2/2013 |
| WO | 2014/022906 A1 | 2/2014 |
| WO | 2014/151680 A1 | 9/2014 |
| WO | 2015/007949 A1 | 1/2015 |

OTHER PUBLICATIONS

International Search Report and Written Opinion received for corresponding Patent Cooperation Treaty Application No. PCT/FI2015/050782, dated Feb. 12, 2016, 15 pages.
Anonymous: "Organic image sensors from NikkoIA: Printed Electronics World", Jul. 11, 2013. Retreived from URL: http://www.printedelectronicsworld.com/articles/5604/orgainc-image-sensors-from-nikkoia.
Anonymous: "How to measure your heart rate on the Galaxy S4, S3, HTC One, LG G2 . . . ". Feb. 26, 2014. Retrieved from interneURL:http://www.androidbeat.com/2014/02/heres-can-measure-heart-rate-galaxy-s4-s3-htc-one-lg-g2-phones/.
Barker, "Motion-Resistant" Pulse Oximetry: A Comparison of New and Old Models, Anesthesia & Analgesia, vol. 95, No. 4, Oct. 2002, pp. 967-972.
Shah et al., "Performance of Three New-Generation Pulse Oximeters During Motion and Low Perfusion in Volunteers", Journal of clinical anesthesia, vol. 24, No. 5, Aug. 2012, pp. 385-391.
"Researchers Develop Highly-Flexible OLED Light Source", Nikkei Technology, Retreived on Jun. 15, 2017, Webpage available at : http://techon.nikkeibp.co.jp/english/NEWS_EN/20130730/295194/.
"Wireless Shirt for Physiological Monitoring", Sensorionline, Retreived on Aug. 19, 2013, Webpage available at : http://mauro-serpelloni.unibs.it/index.php/research/wireless-shirt-for-physiological-monitoring/.
"Bright Future Predicted for Flexible Electronics", ttiinc, Retreived on Jun. 15, 2017, Webpage available at : https://www.ttiinc.com/content/ttiinc/en/resources/marketeye/categories/new-technology/me-slovick-20130130.html.
"Contactless Electrocardiography Now Possible", News Electronics, Retreived on Jun. 15, 2017, Webpage available at : https://electronicsnews.com.au/contactless-electrocardiography-now-possible/.
"New Sensor Sheet Lighter, Softer Than Feather", Nikkei Technology, Retreived on May 19, 2017, Webpage available at : http://techon.nikkeibp.co.jp/english/NEWS_EN/20130726/294563/.
Konstantatos et al., "Hybrid Graphene-Quantum Dot Phototransistors With Ultrahigh Gain", Nature Nanotechnology, May 6, 2012, pp. 1-6.
Klekachev et al., "Electron Accumulation in Graphene by Interaction With Optically Excited Quantum Dots", Physica E: Low-dimensional Systems and Nanostructures, vol. 43, No. 5, Mar. 2011, pp. 1046-1049.
Extended European Search Report received for corresponding European Patent Application No. 14194387.8, dated May 18, 2015, 10 pages.
Office action received for corresponding European Patent Application No. 14194387.8, dated Aug. 3, 2018, 6 pages.

* cited by examiner

Capture image of skin beneath OLED —41

Identify blood carrying regions —43

Illuminate only in regions of blood flow —45

APPARATUS, METHOD AND COMPUTER PROGRAM FOR IDENTIFYING BIOMETRIC FEATURES

RELATED APPLICATION

This application was originally filed as PCT Application No. PCT/FI2015/050782 filed Nov. 11, 2015, which claims priority benefit from EP Patent Application No. 14194387.8 filed Nov. 21, 2014.

TECHNOLOGICAL FIELD

Examples of the present disclosure relate to an apparatus, method and computer program for identifying biometric features. Examples of the present disclosure relate to an apparatus, method and computer program for identifying biometric features wherein the identification of the biometric features may be used to authenticate the user of the apparatus and/or monitor biometric parameters of the user.

BACKGROUND

Wearable electronic devices which may be used to monitor biometric parameters of a user are known. Such devices may be configured to monitor parameters such as heart rate, blood oxygenation, temperature, galvanic skin conductance or any other suitable parameter. These parameters may then be used to track the activity levels of the user or monitor the health and/or well being of the user.

It is useful to provide such devices which are efficient enough to be worn for long periods of the time by the user but which enable efficient capture of the biometric parameter data. It is also useful to be able to associate the information obtained by the device with the identity of the wearer.

BRIEF SUMMARY

According to various, but not necessarily all, examples of the disclosure there may be provided a method comprising: illuminating a portion of skin of a user; detecting light scattered by the illuminated portion of skin and using the detected light to identify locations of biometric features within the illuminated portion of skin; and configuring a light source to selectively illuminate identified locations of biometric features.

In some examples the biometric features may comprise features which enable a user to be uniquely identified.

In some examples the biometric features may comprise blood vessels.

In some examples the method may further comprise configuring a photodetector to selectively detect light scattered from the identified locations of biometric features.

In some examples the selective illumination of biometric features may be used to identify a user. The information obtained from the biometric features may be used to create cryptographic key information which enables a user to be identified.

In some examples the selective illumination of blood vessels may be used to monitor biometric parameters of the user.

In some examples the method may further comprise tuning the intensity of the illumination based on the intensity of the detected scattered light.

In some examples a light source configured to illuminate the skin of the user is also configured to illuminate a display.

In some examples a light source may be configured to be provided adjacent to the skin of the user.

In some examples the light source may comprise a plurality of organic light emitting diodes.

In some examples the scattered light may be detected by a quantum dot detector.

In some examples the areas of the user's skin which are selectively illuminated may have a concentration of biometric features above a threshold.

According to various, but not necessarily all, examples of the disclosure there may be provided an apparatus comprising: processing circuitry; and memory circuitry including computer program code; the memory circuitry and the computer program code configured to, with the processing circuitry, cause the apparatus at least to perform; illuminating a portion of skin of a user; detecting light scattered by the illuminated portion of skin and using the detected light to identify locations of biometric features within the illuminated portion of skin; and configuring a light source to selectively illuminate identified locations of biometric features.

In some examples the biometric features may comprise features which enable a user to be uniquely identified.

In some examples the biometric features may comprise blood vessels.

In some examples the processing circuitry and memory circuitry may be further configured to configure a photodetector to selectively detect light scattered from the identified locations of biometric features.

In some examples the selective illumination of blood vessels may be used to identify a user. The information obtained from the biometric features may be used to create cryptographic key information which enables a user to be identified.

In some examples the selective illumination of blood vessels may be used to monitor biometric parameters of the user.

In some examples the apparatus may be further configured to tune the intensity of the illumination based on the intensity of the detected scattered light.

In some examples a light source configured to illuminate the skin of the user may also be configured to illuminate a display.

In some examples a light source may be configured to be provided adjacent to the skin of the user.

In some examples the light source may comprise a plurality of organic light emitting diodes.

In some examples the scattered light may be detected by a quantum dot detector.

In some examples the areas of the user's skin which are selectively illuminated may have a concentration of biometric features above a threshold.

In some examples there may be provided a wearable electronic device comprising an apparatus as described above.

According to various, but not necessarily all, examples of the disclosure there may be provided a computer program comprising computer program instructions that, when executed by processing circuitry, enable controlling an apparatus to: illuminate a portion of skin of a user; detect light scattered by the illuminated portion of skin and using the detected light to identify locations of biometric features within the illuminated portion of skin; and configure a light source to selectively illuminate identified locations of biometric features.

According to various, but not necessarily all, examples of the disclosure there may be provided a computer program comprising program instructions for causing a computer to perform the methods described above.

According to various, but not necessarily all, examples of the disclosure there may be provided a physical entity embodying the computer program as described above.

According to various, but not necessarily all, examples of the disclosure there may be provided an electromagnetic carrier signal carrying the computer program as described above.

According to various, but not necessarily all, examples of the disclosure there may be provided an apparatus comprising: a light source; a photodetector;

an attachment portion configured to enable the light source and photodetector to be positioned adjacent to a portion of skin of a user; wherein the light source is configured to selectively illuminate portions of the skin of the user based on identified locations of biometric features in the portion of skin of the user.

In some examples the photodetector may be configured to selectively detect light scattered from the identified locations of biometric features.

In some examples the attachment portion may comprise a wrist strap.

In some examples the light source may comprise a plurality of light emitting diodes. The plurality of light emitting diodes may be configured to illuminate a display.

In some examples the photodetector may comprise a quantum dot detector.

According to various, but not necessarily all, examples of the disclosure there may be provided a method comprising: obtaining biometric information of a user by detecting light scattered by biometric features of the user; and generating cryptographic keys from the obtained biometric information wherein the cryptographic keys enable authentication of a user.

In some examples the biometric information may be obtained by imaging a portion of the user's skin.

In some examples the method may further comprise removing correlations in the obtained biometric information to increase the randomness of the information used to generate the cryptographic key.

In some examples the cryptographic keys may be generated from the biometric features of the user in a response to a request for authentication.

In some examples the method may further comprise transmitting at least one of the cryptographic keys over a wireless connection.

In some examples the method may further comprise determining a location of a user.

According to various, but not necessarily all, examples of the disclosure there may be provided an apparatus comprising: processing circuitry; and memory circuitry including computer program code; the memory circuitry and the computer program code configured to, with the processing circuitry, cause the apparatus at least to perform; obtaining biometric information of a user by detecting light scattered by biometric features of the user; and generating cryptographic keys from the obtained biometric information wherein the cryptographic keys enable authentication of a user.

In some examples the biometric information may be obtained by imaging a portion of the user's skin.

In some examples the apparatus may be further configured to remove correlations in the obtained biometric information to increase the randomness of the information used to generate the cryptographic key.

In some examples the cryptographic keys may be generated from the biometric features of the user in a response to a request for authentication.

In some examples the apparatus may be further configured to transmit at least one of the cryptographic keys over a wireless connection.

In some examples the apparatus may be further configured to determine a location of a user.

According to various, but not necessarily all, examples of the disclosure there may be provided a computer program comprising computer program instructions that, when executed by processing circuitry, enable controlling an apparatus to: obtaining biometric information of a user by detecting light scattered by biometric features of the user; and generating cryptographic keys from the obtained biometric information wherein the cryptographic keys enable authentication of a user.

According to various, but not necessarily all, examples of the disclosure there may be provided a computer program comprising program instructions for causing a computer to perform the methods described above.

According to various, but not necessarily all, examples of the disclosure there may be provided a physical entity embodying the computer program as described above.

According to various, but not necessarily all, examples of the disclosure there may be provided an electromagnetic carrier signal carrying the computer program as described above.

According to various, but not necessarily all, examples of the disclosure there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Figure 1:
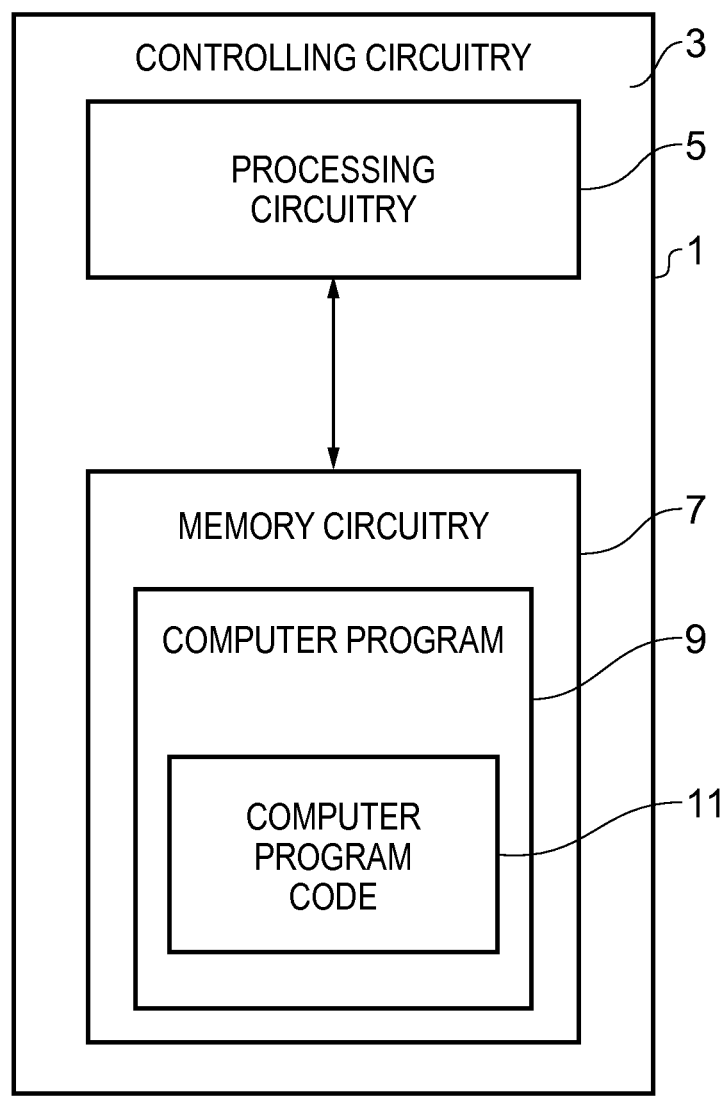
FIG. 1 illustrates an apparatus.

The Figures illustrate methods and apparatus configured to implement the method. The method comprises illuminating 31 a portion of skin of a user; detecting 33 light scattered by the illuminated portion of skin and using the detected light to identify locations of biometric features within the illuminated portion of skin; and configuring 35 a light source 25 to selectively illuminate identified locations of biometric features.

The methods and apparatus provide for an efficient device which may be used to monitor biometric parameters of the user. By selectively illuminating the portions of the skin which contain the biometric features the signal to noise ratio of the signal may be reduced. This may also reduce the power consumption of the apparatus 1.

The apparatus 1 may also be configured to enable a user to be identified. The Figures also illustrate methods and apparatus configured to implement the method wherein the method comprises: obtaining biometric information of a user by detecting light scattered by biometric features of the user; and generating cryptographic keys from the obtained biometric information wherein the cryptographic keys enable authentication of a user.

This may enable the user of the apparatus to be identified. This may enable the biometric information which is obtained to be automatically associated with a user, for example for monitoring the health and wellbeing and/or fitness of the user. In some examples it may be used to enable the user to be authenticated by a third party. The authentication may enable a transaction to be performed or may enable the user to access information or secure locations.

FIG. 1 schematically illustrates an example apparatus 1 which may be used in implementations of the disclosure. The apparatus 1 illustrated in FIG. 1 may be a chip or a chip-set. In some examples the apparatus 1 may be provided within a device such as a wearable electronic device 21. The wearable electronic device 21 may be configured to be attached to a user's body and monitor biometric parameters of the user.

The example apparatus 1 comprises controlling circuitry 3. The controlling circuitry 3 may provide means for illuminating 31 a portion of skin of a user; detecting light scattered by the illuminated portion of skin and using 33 the detected light to identify locations of biometric features within the illuminated portion of skin; and configuring 35 a light source 25 to selectively illuminate identified locations of biometric features.

In some examples where the controlling circuitry 3 may also provide means for obtaining biometric information of a user by detecting light scattered by biometric features of the user; and generating cryptographic keys from the obtained biometric information wherein the cryptographic keys enable authentication of a user.

The processing circuitry 5 may be configured to read from and write to memory circuitry 7. The processing circuitry 5 may comprise one or more processors. The processing circuitry 5 may also comprise an output interface via which data and/or commands are output by the processing circuitry 5 and an input interface via which data and/or commands are input to the processing circuitry 5.

The memory circuitry 7 may be configured to store a computer program 9 comprising computer program instructions (computer program code 11) that controls the operation of the apparatus 1 when loaded into processing circuitry 5. The computer program instructions, of the computer program 9, provide the logic and routines that enable the apparatus 1 to perform the example methods illustrated in FIGS. 3, 4 and 12 to 13. The processing circuitry 5 by reading the memory circuitry 7 is able to load and execute the computer program 9.

The apparatus 1 therefore comprises: processing circuitry 5; and memory circuitry 7 including computer program code 11, the memory circuitry 7 and the computer program code 11 configured to, with the processing circuitry 5, cause the apparatus 1 at least to perform: illuminating a portion of skin of a user; detecting light scattered by the illuminated portion of skin and using the detected light to identify locations of biometric features within the illuminated portion of skin; and configuring a light source 25 to selectively illuminate identified locations of biometric features.

In some examples the apparatus 1 may comprise: processing circuitry 5; and memory circuitry 7 including computer program code 11, the memory circuitry 7 and the computer program code 11 configured to, with the processing circuitry 5, cause the apparatus 1 at least to perform: obtaining biometric information of a user by detecting light scattered by biometric features of the user; and generating a cryptographic key from the obtained biometric information wherein the cryptographic key enables authentication of a user.

The computer program 9 may arrive at the apparatus 1 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 9. The apparatus may propagate or transmit the computer program 9 as a computer data signal. In some examples the computer program code 11 may be transmitted to the apparatus 1 using a wireless protocol such as Bluetooth, Bluetooth Low Energy, Bluetooth Smart, 6LoWPan ($IP_v6$ over low power personal area networks) Zig Bee, ANT+, near field communication (NFC), Radio frequency identification, wireless local area network (wireless LAN) or any other suitable protocol.

Although the memory circuitry 7 is illustrated as a single component in the figures it is to be appreciated that it may be implemented as one or more separate components some or all of which may be integrated/removable and/or may provide permanent/semi-permanent/dynamic/cached storage.

Although the processing circuitry 5 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware.

The term "circuitry" would also cover, for example and if applicable to the particular claim element, a baseband integrated circuit or applications processor integrated circuit for a mobile phone or a similar integrated circuit in a server, a cellular network device, or other network device.

Figure 2:
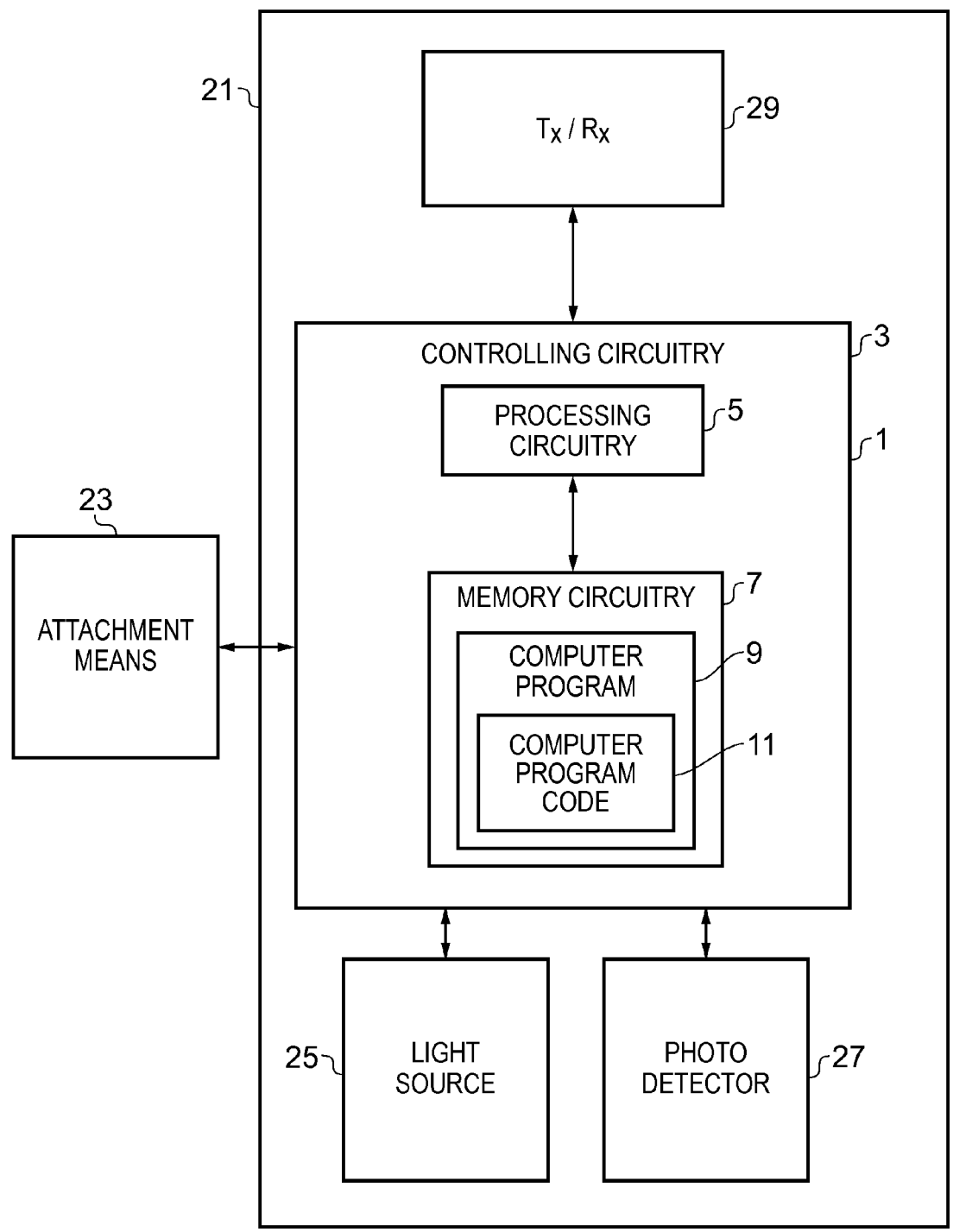
FIG. 2 illustrates an electronic device comprising an apparatus.

FIG. 2 schematically illustrates an electronic device 21. The electronic device 21 comprises an apparatus 1 as described above. Corresponding reference numerals are used for corresponding features. The example electronic device 21 of FIG. 1 also comprises attachment means 23, at least one light source, 25, at least one photodetector 27 and at least one transceiver 29. It is to be appreciated that only features which are needed for the following description are illustrated in FIG. 2. The electronic device 21 may comprise other features which are not illustrated in FIG. 2 such as a display, power source or any other suitable features.

The electronic device 21 may be a wearable electronic device which may be configured to be worn by the user. In such examples the attachment means 23 may comprise any means which may enable the electronic device 21 to be secured to the user's body. In some examples the attachment means 23 may comprise a strap which may be attached around a part of the body of the user such as the user's arm, leg or chest. In other examples the attachment means 23 may comprise an adhesive portion which may enable the electronic device 21 to be adhered to the user's skin. In some examples the electronic device 21 may be part of an item of clothing or a head set which may be configured to be worn by the user.

In some examples the electronic device 21 may be flexible. This may enable the electronic device 21 to be fitted to the shape of the user's body. In some examples the electronic device 21 may comprise flexible portions and rigid portions. The flexible portions may enable the electronic device 21 to be attached to the user's body while the rigid portions may be used to protect sensitive electronic components within the electronic device 21.

The light source 25 may comprise any means which may be configured to illuminate a portion of the skin of the user.

In examples of the disclosure the light source 25 may be configured so that the light signal provided by the light source 25 may be controlled. The light signal may be controlled by the controlling circuitry 3. The light signal may be controlled to enable biometric features to be detected and to enable selective illumination of areas within the portion of skin of the user. The location, wavelength, brightness or any other parameter of the light signal may be controlled.

In some examples the light source 25 may comprise a plurality of light emitting diodes (LEDs), a plurality of organic light emitting diodes (OLEDs), or any other suitable means. The plurality of diodes may be arranged in an array. The array of diodes may be configured so that diodes within the array can be selectively illuminated. In some examples the controlling circuitry 3 may be configured to control which of the diodes are illuminated and which of the diodes are not illuminated.

In some examples the light source 25 may be flexible. This may enable the light source to be fitted to the body of the user. For instance the light source may comprise a plurality of flexible OLEDs. In other examples the LEDs or OLEDs may be rigid, however a plurality of rigid diodes may be provided on a flexible substrate. The flexible substrate may allow for relative movement of the diodes which may enable the light source to be fitted to the body of a user.

In some examples the light source 25 may be positioned within the electronic device 21 so that when the electronic device 21 is attached to the body of the user the light source 25 is adjacent to the skin of the user. In some examples the attachment means 23 may be configured to ensure that the light source 25 is held tightly against the skin of the user. This may reduce measurement errors which could be caused by movement of the electronic device 21 or by ambient light reaching the portion of skin underneath the electronic device 21.

In some examples the light source 25 may be configured to provide light to other components within the electronic device 21. For instance, in some examples the light source 25 may also be configured to illuminate a display.

The photodetector 27 may comprise any means which may be configured to detect light which is reflected back from the portion of skin which is illuminated by the user. In some examples the light may be scattered by biometric features of the user.

In some examples the photodetector 27 may comprise a quantum dot photodetector. In the quantum dot photodetector, the quantum dots are configured to provide sensitivity to a specific wavelength. The quantum dot photodetector may also be configured to provide an increased dynamic range of detection at that wavelength. This may enable the apparatus 1 to operate with a lower intensity of illumination. This may also provide more robust data capture if the illumination level varies over a large intensity range. This could occur, for instance, if the apparatus 1 moves relative to the user.

In some examples the photodetectors 27 may be integrated within the light source 25. For instance the light source 25 may comprise an array of diode pixels and the photodetector pixels may be provided within the array. Examples of photodetectors 27 integrated within the light source 25 are provided below with reference to FIGS. 5 to 11B.

The light source 25 and the photodetector 27 may be configured to enable biometric features of the user to be identified. The biometric features may comprise any features which may enable the user to be uniquely identified. In some examples the biometric features may enable biometric parameters of the user to be monitored. In some examples the biometric features may comprise blood vessels. The blood vessels may comprise veins, venules, arteries, arterioles or capillaries. The blood vessels may enable biometric parameters such as heart rate, blood pressure or blood oxygen levels to be monitored. As red blood cells strongly absorb light detecting the reflected signal which is detected by the photodetectors 27 will change as the blood volume in the illuminated portion of the user changes.

The transceiver 29 may comprise one or more transmitters and/or receivers. The transceiver 29 may comprise any means which enables the electronic device 21 to establish a communication connection with one or more other devices and exchange information with the other devices.

In some examples the communication connection may be a wireless communication connection. The wireless communication connection may be a secure wireless communication connection. In some examples the wireless communication connection may be a low power communication connection such as Bluetooth, Bluetooth Low Energy, Bluetooth Smart, 6LoWPan (IPv6 over low power personal area networks), ZigBee, ANT+, near field communication (NFC), wireless LAN or any other suitable means.

In some examples the other device could be a remote device. For example the remote device could be a payment and/or authentication terminal which may require authentication of the user. In some examples the other device could be a user device such as a mobile phone, tablet, personal computer or other personal device. In such examples the transceiver 29 may be configured to enable information to be exchanged between the electronic devices 21 and the other devices to enable authentication of the user.

In some examples the other device could be one or more other wearable electronic devices. The other wearable electronic devices may be attached to different parts of the user's body. In such examples the transceiver 29 may be configured to enable information to be exchanged between the different wearable electronic devices 21. This may enable biometric parameters to be monitored at different parts of the user's body.

In some examples the transceiver 29 may be configured to enable location of the electronic device 21 to be determined. For instance, the transceiver 29 may be configured for Bluetooth communication. Fixed location Bluetooth devices may be provided within a defined space such as a room, domestic dwelling, commercial space or other suitable space. Triangulation of the signals transmitted between the devices may be used to determine the location of the electronic device 21. In some examples the electronic device 21 may be configured to enable high accuracy indoor positioning (HAIP) or any other suitable positioning protocol. This enables a location of the user to be identified and may enable the tracking of individual users within given spaces.

The transceiver 29 may be configured to provide information obtained via the transceiver 29 to the controlling circuitry 3. The transceiver 29 may also be configured to enable information from the controlling circuitry 3 to be transmitted via the transceiver 29.

Figure 3:
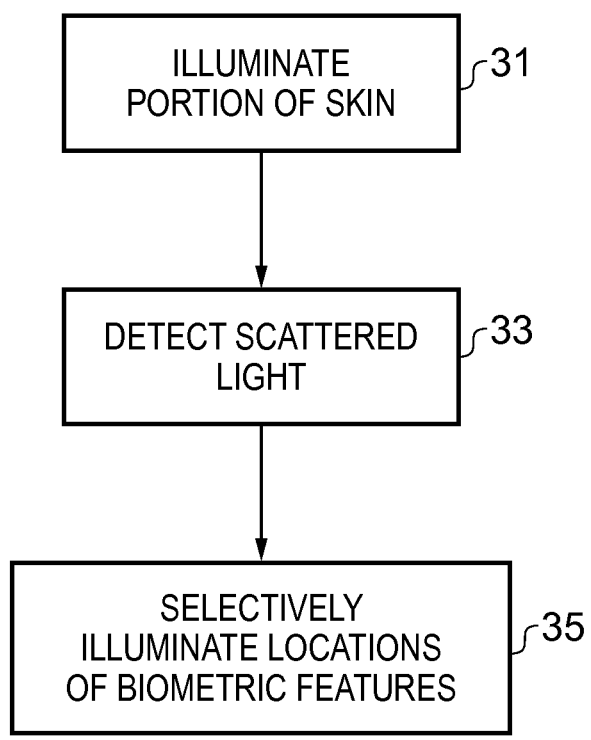
FIG. 3 illustrates a method.

FIG. 3 illustrates a method. The example method may be implemented using an apparatus 1 and electronic device 21 as described above. Corresponding reference numerals are used to refer to corresponding features.

The method comprises, at block 31, illuminating a portion of skin of a user. The method also comprises, at block 33, detecting light scattered by the illuminated portion of skin and using the detected light to identify locations of biometric features within the illuminated portion of skin. At block 35 the method comprises configuring a light source 25 to selectively illuminate identified locations of biometric features.

Figure 4B:
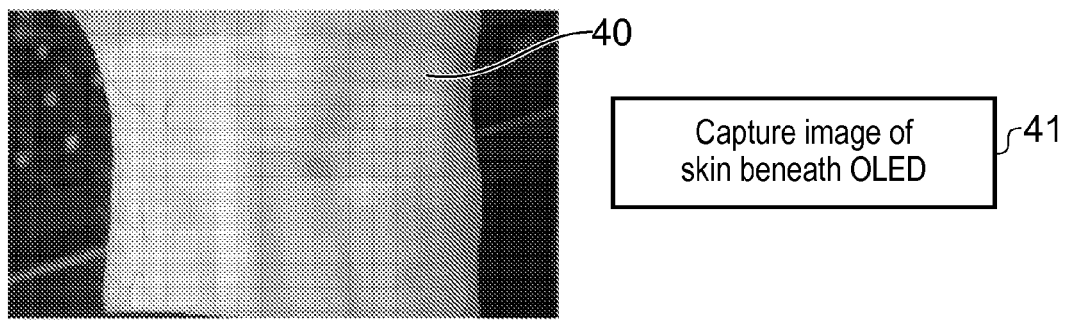
FIGS. 4A to 4D illustrate another method.
Figure 4C:
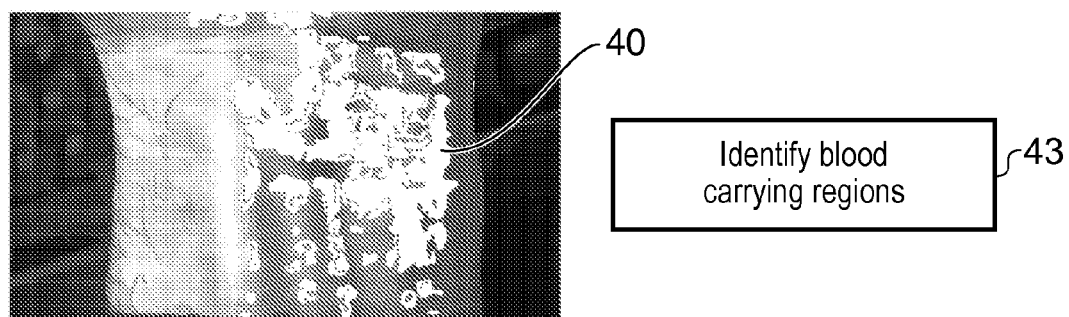
Figure 4D:
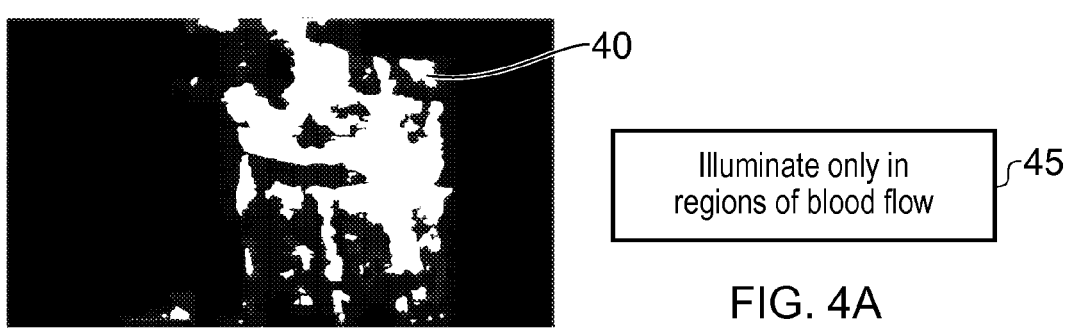
Figure 4A:
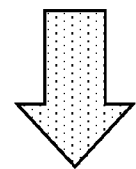
Figure 4A:
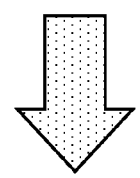

FIGS. 4A to 4C illustrate another method which may be implemented using an apparatus 1 and electronic device 21 as described above. FIG. 4A illustrates an example method and FIGS. 4B to 4D show example portions of the skin of the user.

In the example of FIGS. 4A to 4C the electronic device 21 is attached to the wrist 40 of the user. In such examples the electronic device 21 may comprise a strap which may be wrapped around the wrist 40 of the user in the manner of a watch or bracelet.

At block 41 an image of the skin underneath the light source 25 is captured. In order to capture the image the light source 25 may illuminate all of the skin underneath the light source 25. In some examples the illumination of the user's skin may be uniform so that each area of the portion of the skin underneath the light source 25 receives the same amount of light.

It is to be appreciated that in some examples more than one image may be obtained in order to enable the biometric features to be identified. For instance, in some examples the electronic device 21 may be configured to use different wavelengths and/or different intensities of light to capture a plurality of images. The different intensities of light may penetrate the tissues of the user to different levels. This may enable different biometric features to be identified.

FIG. 4B shows an example of the portion of skin which may be imaged at block 41. In this particular example the portion of skin comprises the inner wrist 40 of the user. This portion of skin may have a high density of blood vessels close to the surface of the skin.

At block 43 the captured image is analysed to identify and locate biometric features within the captured image. Any suitable means may be used to identify and locate the biometric features. In some examples the biometric features may be identified by using photodetectors 27 arranged into a large area array. The photodetectors 27 may be sensitive to light which is absorbed and re-emitted, scattered or reflected by the biometric features. The positions of the photodetectors 27 which detect scattered light may be used to locate the biometric features of the user.

In the particular example of FIGS. 4A to 4C the electronic device 21 is configured to identify and locate blood vessels within the illuminated portion of skin. This enables the blood carrying regions underneath the light source 25 to be identified. In some examples the electronic device 21 may be configured to detect any blood vessels. In other examples the electronic device 21 may be configured to detect particular types of blood vessels. For instance the electronic device 21 may detect veins, arteries and capillaries. It is to be appreciated that other biometric features may be used in other examples of the disclosure.

It is to be appreciated that any suitable method may be used to determine the optimum location for the selective illumination. For instance in another example the optimum location for the selective illumination may be determined by illuminating different portions of the light source 25 successively. As an example an outer ring of pixels of the light source 25 are illuminated and the response detected by the photodetectors 27 is measured. The illuminated ring of pixels is then moved one row closer to the centre of the array and the response is measured again. The process is repeated until the illumination reaches the centre of the array. The signal to noise ratio is measured in each case, to determine the optimum position for the illumination.

FIG. 4C shows an example of the portion of skin in which the locations of the blood vessels have been identified.

At block 45 the light source 25 is configured to selectively illuminate the identified locations of the biometric features. In the example of FIGS. 4A to 4C the locations of the largest blood vessels are illuminated. This corresponds to the regions of high blood flow. In some examples the areas of the user's skin which are selectively illuminated have a concentration of biometric features above a threshold.

At block 45 the controlling circuitry 3 may identify the portions of the light source 25 which are overlying the regions of high blood flow and then control the light source 25 so that only these regions are illuminated.

FIG. 4D shows an example of the portion of skin which is illuminated at block 45.

The illumination of the skin at block 45 may be used to monitor biometric parameters of the user. For instance the illumination may be used to obtain photoplethysmogram (PPG) measurements which may be used to monitor heart rate and/or blood oxygen levels. As the regions identified as having high blood flow are illuminated at block 45 this increases the signal to noise ratio for the measurements of the biometric parameters.

In other examples the illumination of the skin at block 45 may be used to obtain information which can be used to authenticate a user.

In the example of FIGS. 4A to 4D the region of largest blood flow is selectively illuminated. In other examples the regions of low blood flow may be illuminated. For instance the electronic device 21 may be configured to identify the locations of the largest blood vessels and then selectively illuminate the locations which do not contain the large blood vessels. This may enable the selective illumination of regions of tissue that contain narrow blood vessels such as capillaries. Illuminating these regions may enable accurate measurements of a user's heart rate because the narrow blood vessels show a large change in volume of blood with each pulse. The large change in volume can be detected as a large change in the amount of light absorbed by these regions.

In some examples the electronic device 21 may be configured to obtain a map of the oxygen rich arteries and arterioles and the oxygen poor veins and venules and differentiate between these complementary pathways in the circulatory system to enable for more accurate blood oxygenation measurements to be made.

In the example of FIGS. 4A to 4D the light source 25 is selectively illuminated to illuminate selected portions of the skin of the user. In some examples the photodetector 27 may be configured to selectively detect light scattered from the identified locations of biometric features. In some examples the photodetector 27 may be configured to detect specific wavelengths of light which may correspond to light which is scattered by the biometric features. In some examples only portions of the photodetector 27 overlaying the portions of skin of the user that are illuminated might be activated.

In some examples the electronic device 21 may be configured to tune the intensity of the illumination provided by the light source 25 based on the intensity of the detected scattered light. This may enable the power consumed by the light source 25 to be reduced but still ensure that an accurate signal is provided by the photodetector 27.

Figure 5:
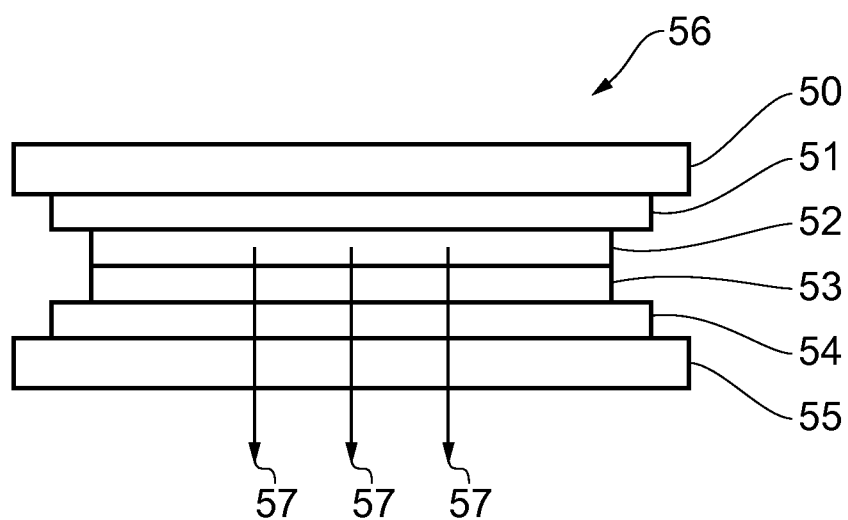
FIG. 5 illustrates an example OLED (organic light emitting diode) structure.

FIG. 5 illustrates an example OLED structure 56 which may be used to provide a light source 25 in some examples of the disclosure.

The example OLED structure 56 comprises a top substrate 50, a cathode layer 51, a light emissive layer 52, a hole transport layer 53, an anode layer 54 and a bottom substrate 55.

The top substrate 50 may comprise a transparent flexible polymer material. The material may be transparent to enable light to pass through the top substrate 50. In some examples the top substrate 50 may be coated with a barrier material. The barrier material may be arranged to prevent fluid ingress such as water or oxygen or other contaminants. The barrier material may improve the lifetime of the OLED structure 56.

The cathode layer 51 is provided underneath the top substrate 50. The cathode layer 51 may comprise any means which may be configured to supply electrons to the light emissive layer 52. The cathode layer 51 may comprise any suitable conductive material. The conductive material may comprise a metal with a low work function such as Calcium, Lithium, Aluminium, Silver, Barium Lithium Fluoride or any other material or combination of these materials.

The cathode layer 51 may be a thin layer. In some example the cathode layer 51 may be between 50-500 nm thick.

The light emissive layer 52 is provided underneath the cathode layer 51. The light emissive layer 52 may comprise any material in which electrons and holes combine to emit photons. The light which is emitted by the light emissive layer 52 is indicated by the arrows 57 in FIG. 5.

In some examples the material used in the light emissive layer 52 may comprise polyfluorenes, polyphenylene vinylenes, organic transition metal small molecule compounds or any other suitable material.

The light emissive layer 52 may be a thin layer. In some example the light emissive layer 52 may be between 20-200 nm thick.

The hole transport layer 53 is provided underneath the light emissive layer 52. The hole transport layer 53 may comprise any means which may transfer positive charge from the anode layer 54 to the light emissive layer 52. In some examples the material used in the hole transport layer 53 may comprise p-doped or oxidized conductive materials or any other suitable material.

The hole transport layer 53 may be a thin layer. In some example the hole transport layer 53 may be between 20-200 nm thick.

The anode layer 54 is provided underneath the hole transport layer 53. The anode layer 54 may be configured to provide electron holes to the hole transport layer 53. The anode layer 54 may be transparent. The anode layer 54 may comprise any suitable materials such as Indium Tin Oxide, fluorine doped Tin Oxide (FTO), Zinc Oxide (ZnO), fine wire metal grids patterned from conductive material such as Copper or Silver, Silver nano-wires, Carbon nanotubes (CNT), graphene, metal doped graphene or any other suitable material.

The bottom substrate 55 is provided underneath the anode layer 54. The bottom substrate may also comprise a transparent flexible polymer material. The bottom substrate 55 may also have a barrier coating. The top substrate 50 and the bottom substrate 55 may encapsulate the OLED structure 56.

The top substrate 50 and the bottom substrate 55 may be flexible substrates. The top substrate 50 and the bottom substrate 55 may comprise any suitable material such as Polyethylene 2, 6-naphthalate (PEN). Polyethylene Terephthalate (PET), Polyimide (PI), Polycarbonate (PC), Polyethylene (PE), Polyurethane (PU), Polymethylmethacrylate (PMMA), Polystyrene (PS), natural rubbers such as; Polyisoprenes, Polybutadienes, Polychloraprenes, Polyisobutylenes, Nitrile Butadienes and Styrene Butadienes, saturated elastomeric materials such as; Polydimethylsiloxane (PDMS), Silicone rubbers, Fluorosilicone rubbers, Fluoroelastomers, Perfluoroelastomers, Ethylene Vinyl Acetate (EVA) Thermoplastic Elastomers such as Styrene Block copolymers, Thermoplastic polyolefins, Thermoplastic vulcanisates, Thermoplastic Polyurethane (TPU) Thermoplastic Copolyesters, Melt processable rubbers or any other suitable material.

In some examples the substrates 50, 55 may comprise metal foils such as planar metal foils. Components such as thin film transistors and displays may be provided on the metal foils.

In some examples the substrates 50, 55 may comprise flexible displays such as Organic Light Emitting Diodes (OLED), Liquid Crystal (LCD), Polymer Dispersed Liquid Crystal (PDLC) or other reflective LCD display, Electro-Phoretic (EP), Electroluminescent (EL), Electrowetting (EW) Electrochromical (EC), or displays which use other optical modulation effects such as Interference based on frustrated internal reflection or Fabry Perot cavities.

In some examples the substrates 50, 55 may comprise a touch sensitive layer. The touch sensitive layer may use any suitable sensing means such as resistive, optical or capacitive touch sensing. In some examples the touch sensitive layer may be included as part of a display. In other examples the touch sensitive layer may be separate to the display.

In some examples the touch sensitive layer may comprise conductive patterns of transparent conducting metal oxides such as Indium Tin Oxide (ITO), Fluorine doped tin oxide (FTO), Aluminium doped zinc oxide (AlZnO), Poly(2,3-dihydrothieno-1,4-dioxin)-poly(styrenesulfonate) (PEDOT:PSS), Polypyrrole (Ppy), Silver nanowires, Carbon Nanotubes and Graphene based materials including composites thereof Graphene or any other suitable material or arrangements of material.

Figure 6:
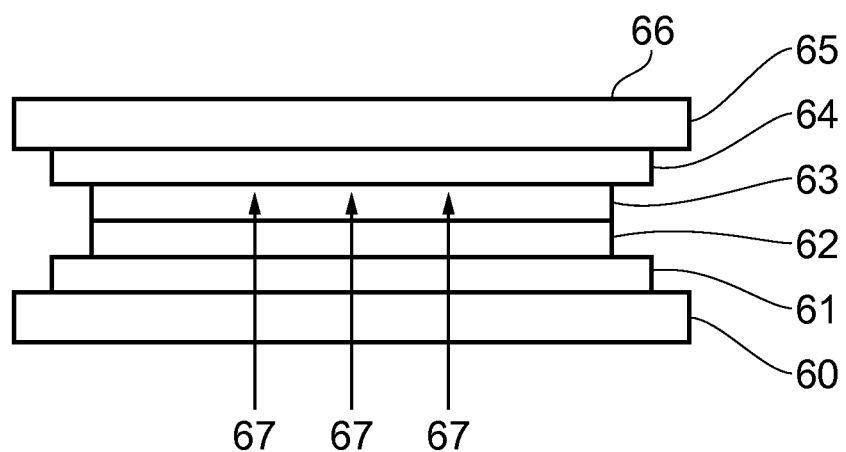
FIG. 6 illustrates an example OPV (organic photo-voltaic) structure.

FIG. 6 illustrates an example OPV (organic photo-voltaic) structure 66 which may be used to provide a photodetector in some examples of the disclosure.

The example OPV structure 66 comprises a first substrate 60, an anode layer 61, a light sensitive layer 62, a hole transport layer 63, a cathode layer 64 and a second substrate 65.

The first substrate 60 may comprise a transparent flexible polymer material. The material may be transparent to enable light to pass through the top first substrate 60. In some examples the first substrate 60 may be coated with a barrier material. The barrier material may be arranged to prevent fluid ingress such as water or oxygen or other contaminants. The barrier material may improve the lifetime of the OPV structure 66.

The anode layer 61 is provided overlaying the first substrate 60. The anode layer 61 may be configured to extract electrons from the light sensitive layer 62. The anode layer 61 may be transparent. The anode layer 61 may comprise any suitable materials such as Indium Tin Oxide, fluorine doped Tin Oxide (FTO), Zinc Oxide (ZnO), fine wire metal grids patterned from conductive material such as Copper or Silver, Silver nano-wires, Carbon nanotubes (CNT), graphene, metal doped graphene or any other suitable material.

The light sensitive layer 62 is provided overlaying the anode layer 61. The light sensitive layer 62 in which electron and hole pairs are generated by incident photons. The incident light is indicated by the arrows 67 in FIG. 6.

The light sensitive layer 62 may comprise any suitable material. The light sensitive layer may comprise n-type materials, or p-type materials, or a mixture of both n-type and p-type materials. Examples of p-type materials which may be used comprise polythiophene, polypyrrole, polyaniline, polyfluorene, polyphenylene vinylene, polyphenylene. Examples of n-type materials which could be used comprise fullerenes, dithieno [3, 2-b:2', 3'-d]pyrrole (DTP), poly('substituted dithieno[3, 2-b: 2', 3'-d]pyrrole)s (PDTPs)

The light sensitive layer 62 may be between 70-300 nm thick.

The hole transport layer 63 is provided overlaying the light sensitive layer 62. The hole transport layer 63 may comprise any means which may extract electron holes from the light sensitive layer 62 to the cathode layer 64. In some examples the material used in the hole transport layer 63 may comprise p-doped or oxidized conductive materials or any other suitable material.

The hole transport layer 63 may be a thin layer. In some examples the hole transport layer 63 may be between 20-200 nm thick.

The cathode layer 64 is provided overlaying the hole transport layer 63. The cathode layer 64 may comprise any means which may be configured to extract electron holes from the hole transport layer 63. The cathode layer 64 may comprise any suitable conductive material. The conductive material may comprise a metal with a low work function such as Calcium, Lithium, Aluminium, Silver, Barium Lithium Fluoride or any other material or combination of these materials.

The cathode layer 61 may be a thin layer. In some example the cathode layer 61 may be between 50-500 nm thick.

The second substrate 65 is provided overlaying the cathode layer 64. The bottom substrate may also comprise a transparent flexible polymer material. The second substrate 65 may also have a barrier coating. The top substrate 65 and the second substrate 65 may encapsulate the OPV structure 66.

Figure 7:
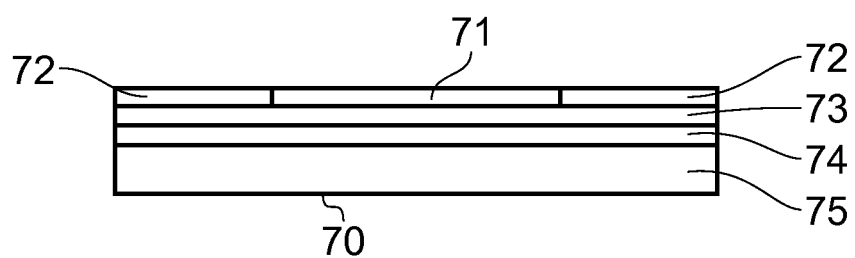
FIG. 7 illustrates an example quantum dot photo detector structure.

FIG. 7 illustrates an example quantum dot photodetector structure 70 which may be used in some examples of the disclosure. The example structure of FIG. 7 is a hybrid graphene-quantum dot photodetector structure 70. The example quantum dot photo detector structure 70 comprises a conductive substrate 75, a dielectric layer 74, a charge transport layer 73, source and drain electrodes 72 and a quantum dot layer 71.

The conductive substrate 75 may comprise any suitable material such as Si, GaAs, Boron Nitride or any other suitable material.

The dielectric layer 74 is provided overlaying the conductive substrate 75. The dielectric layer 74 may comprise any suitable material such as $SiO_2$, LiF, Alumina, Hafnium oxide, a flexible transparent polymer or any other flexible insulating material.

The charge transport layer 73 is provided overlaying the dielectric layer 74. The charge transport layer 73 may comprise any suitable conductive material. In a hybrid graphene-quantum dot photodetector structure 70 the charge transport layer may comprise a graphene layer. In some examples other carbon-based materials may be used such as reduced graphene oxide, carbon nanotubes (CNTs) or any other suitable material.

The quantum dot layer 71 may be very thin. In some examples the quantum dot layer 71 may be two dimensional. In some examples the thickness of the quantum dot layer 71 may be of the order of 200 mm. This may allow for optimal charge transfer.

The quantum dot layer 71 may be configured to be sensitive to a particular frequency of electromagnetic radiation. In some examples the quantum dot layer 71 may be configured to be sensitive to infra red radiation. In such examples the materials used for the quantum dot layer 71 may comprise: CdSe, CdS, PbSe, PbS, ZnO, ZnS, CZTS, $Cu_2S$, $Bi_2S_3$, $Ag2S$, HgTe, CdSe, CdHgTe, InAs, InSb, Ge, CIS or any other suitable material.

The size of the quantum dot layer 71 may be dependent upon the material which is used and the wavelength of light which is to be detected.

The quantum dot layers 71 may be attached to each other. In some examples the quantum dot layers 71 may be attached to the charge transport layer 73. The respective quantum dot layers 71 and the charge transport layers may be connected to each other by a ligand which may stabilise or cross-link the quantum dot layers 71 to forma conductive solid. In some examples the ligands may comprise ethanedithiol, ethylene diamine, ethanethiol, propanethiol, benzenedithiol, hydrazine, formic acid, oxalic acid, acetic acid, or inorganic moieties such as $SnS4$, $PbBr2$, $PbI2$, $PbCl2$.

The coupling of the quantum dot layer 71 to the charge transport layer 73 enables excitons generated in the quantum dot layer 71 to be separated into electron-hole pairs and either the holes or electrons are removed by the charge transport layer 73.

In some examples the quantum dot photodetector structure 70 may comprise an additional photosensitive semiconductor material. The additional photosensitive semiconductor material may increase the photosensitivity of the quantum dot photodetector structure 70. The additional photosensitive semiconductor material may comprise a conjugated polymer or dye or any other suitable material.

The quantum dot photodetector structure 70 may have very high levels of sensitivity and gain. The high sensitivity of the quantum dot photodetector structure 70, particularly at infra red wavelengths, enables measurements to be made over large areas with low power input.

Figure 8:
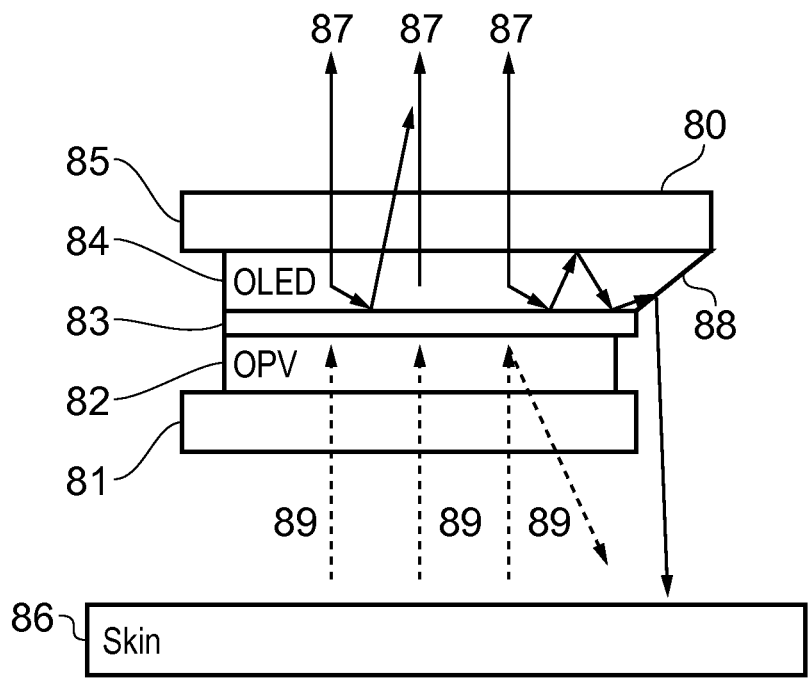
FIG. 8 illustrates an example OLED/OPV display module pixel.

FIG. 8 illustrates an example OLED/OPV display module pixel 80 which may be used in some examples of the disclosure. In the example of FIG. 8 the OLED and OPV structures are stacked overlaying each other. The display module pixel 80 may be arranged within a wearable electronic device 21 so that in use the display module pixel 80 is positioned adjacent to the skin 86 of the user.

The display module pixel 80 of FIG. 8 comprises a first substrate 81, a second substrate 85, an OLED layer 84, and OPV layer 82 and a common cathode 83. The substrates 81, 85 may be flexible substrates which may be configured to encapsulate the OPV layer 82 and the OLED layer 84.

The OPV layer 82 may be as described above with reference to FIG. 6.

The OLED layer 84 may be as described above with reference to FIG. 5. In the example of FIG. 8 the OLED layer 84 is arranged so that the light 87 generated by the OLED layer 84 is emitted vertically and the cathode is at the bottom of the stack. This may enable the light generated by the OLED to be used to illuminate components of the electronic device 21 such as a display or user interface.

The OLED layer 84 also comprises a light guide 88. The light guide 88 may comprise any means which may be configured to guide light from the OLED layer 84 towards the skin 86 of the user. In the example of FIG. 8 the light guide 88 comprises a prismatic reflector which extends over an edge of the cathode layer 83 and OPV layer 82. This enables light form the OLED layer to be used to illuminate both a display, or other components, and the skin 86 of the user.

The OLED/OPV display module pixel 80 may be configured to measure biometric parameters, such as pulse rate, using optical plethysmography (PPG), The OLED/OPV display module pixel 80 may be configured to emit photons 87 light generated by the OLED layer 84 towards the users skin. The OPV layer 82 may be used to capture the photons 89 of light which are reflected.

Figure 9:
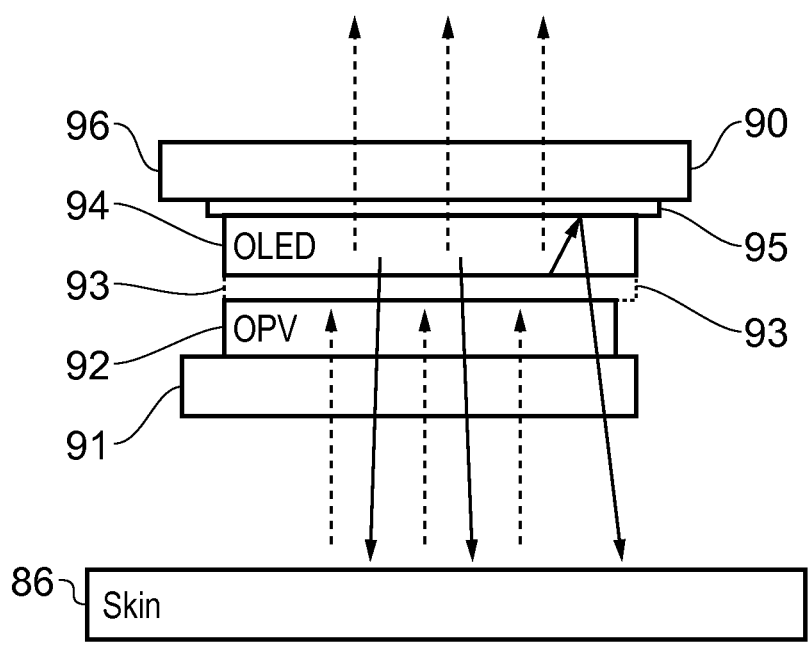
FIG. 9 illustrates another example OLED/OPV display module pixel.

FIG. 9 illustrates another example OLED/OPV display module pixel 90 which may be used in some examples of the disclosure. In the example of FIG. 9 the OLED and OPV structures are stacked overlaying each other. The display module pixel 90 may be arranged within a wearable electronic device 21 so that in use the display module pixel 90 is positioned adjacent to the skin 86 of the user.

The display module pixel 90 of FIG. 9 comprises a first substrate 91, a second substrate 96, an OLED layer 94, and OPV layer 92 and a common cathode 93. The substrates 91, 96 may be flexible substrates which may be configured to encapsulate the OPV layer 92 and the OLED layer 94.

The OPV layer 92 may be as described above with reference to FIG. 6. The OPV layer may be configured to be transparent to light of a first wavelength but configured to absorb light of a second wavelength. This may enable light which is emitted by the OLED layer 94 to pass through the OPV layer on the way to the users skin but enables the reflected light to be absorbed.

The OLED layer 94 may be as described above with reference to FIG. 5. In the example of FIG. 9 the OLED layer 94 is arranged so that the light 97 is emitted vertically and the cathode is at the bottom of the stack. This may enable the light generated by the OLED to be used to illuminate components of the electronic device 21 such as a display or user interface.

In the example of FIG. 9 the display module pixel 90 is configured to enable a portion of the light generated by the OLED layer 94 to be emitted towards the users skin 86 and another portion of the light to be used to illuminate a display or other feature of the electronic device 21. In the example of FIG. 9 the OLED layer 94 comprises a partially reflective upper conductive layer 95. The partially reflective upper conductive layer 95 is configured to allow some of the light 97 to pass through while the rest of the light 97 is reflected down towards the user's skin 86.

The common cathode layer 93 may be transparent. This may enable the light that is emitted by the OLED layer 94 to be transmitted though the display module pixel 90 to the user's skin 86.

The example OLED/OPV display module pixel 90 may be configured to enable light generated by the OLD layer 94 to be used both form monitoring biometric parameters and for illuminating a user interface.

Figure 10:
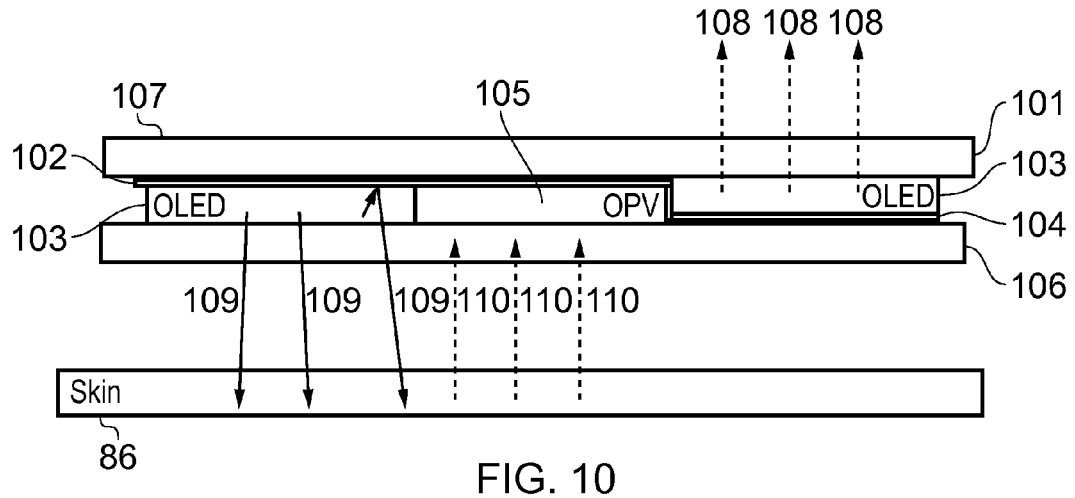
FIG. 10 illustrates a combined OLED/OPV display.

FIG. 10 illustrates a portion of a combined OLED/OPV display 101. The display 101 comprises substrates 106, 107, a plurality of OLED pixels 103 and a plurality of OPV pixels 105. The OLED pixels 103 and OPV pixels 105 may be as described above. It is to be appreciated that other types of light source 25 and photodetector 27 may be used in other examples.

In the example of FIG. 10 the OLED pixels 103 and the OPV pixels 105 are provided adjacent to each other rather than stacked on top of each other. The OLED pixels 103 and the OPV pixels 105 may be arranged in a horizontal array. The OLED pixels 103 and the OPV pixels 105 may be arranged alternately in a horizontal array.

In the example of FIG. 10 the plurality of OLED pixels 103 provide a light source 25. The OLED pixels 103 comprise a reflective cathode 102, 104. Some of the OLED pixels have the reflective cathode 102 positioned at the top of the OLED pixel 103. In the example of FIG. 10 the OLED pixel 103 on the left hand side has the reflective cathode 102 positioned at the top of the OLED pixel 103. This enables light 109 which is provided by the OLED pixel 103 to be directed towards the user's skin. Other OLED pixels 103 within the display 101 have the reflective cathode 104 provided at the bottom of the OLED pixel 103. In the example of FIG. 10 the OLED pixel 103 on the right hand side has the reflective cathode 104 positioned at the bottom of the OLED pixel 103. This enables light 108 which is provided by the OLED pixel 103 to be directed through the top of the display. This enables the display 101 to be used to illuminate user interface devices and also to enable biometric parameters to be measured.

The plurality of OPV pixels 105 may be provided between the OLED pixels and configured to detect the light 110 which is reflected by user's skin 86. This enables biometric features of the user to be identified and biometric parameters to be measured.

The number of OLED pixels 103 and OPV pixels 105 used in the display 101 may depend on the resolution requirements of the display or other user interface elements and/or the spatial sampling needed to obtain the measurements of the biometric parameters.

Figure 11A:
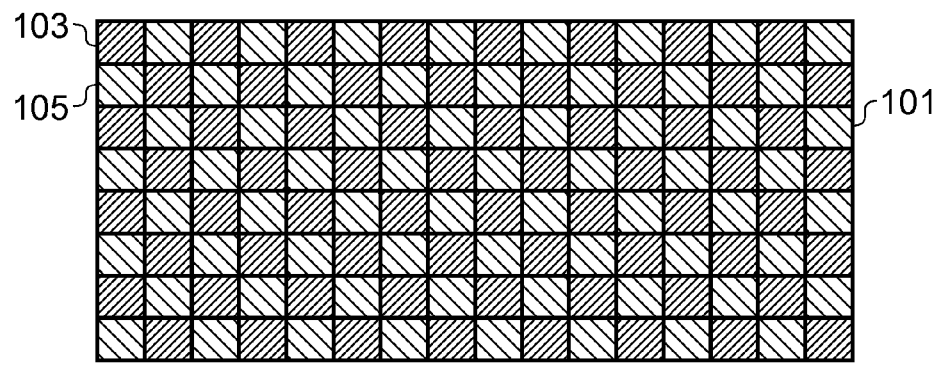
FIGS. 11A and 11B illustrate example pixel arrangements.
Figure 11B:
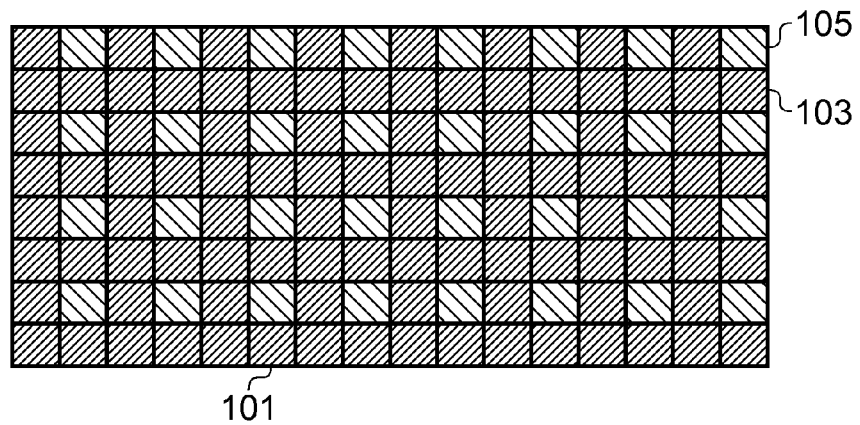

FIGS. 11A and 11B illustrate example pixel arrangements which may be used in a display 101 such as the display 101 of FIG. 10. In each example the display 101 comprises a plurality of OLED pixels 103 and a plurality of OPV pixels 105. In the examples of FIG. 11A and 11B the OLED pixels 103 have darker shading and the OPV pixels 105 have lighter shading.

In the example display 101 of FIG. 11A there are an equal number of OLED pixels 103 and OPV pixels 105. The OLED pixels 103 and OPV pixels 105 are distributed uniformly across the display 101. The OLED pixels 103 and OPV pixels 105 are provided in an alternating pattern across the rows and columns of the display 101.

In the example display 101 of FIG. 11B there are more OLED pixels 103 than OPV pixels 105. In the particular example of FIG. 11B a first row comprises alternating OLED pixels 103 and OPV pixels 105. The second row, which is adjacent to the first row comprises only OLED pixels 103. This pattern is repeated across the display 101. It is to be appreciated that other arrangements of the pixels could be used in other examples of the disclosure.

In other examples there may be provide more OPV pixels 105 than OLED pixels 103.

In the examples of FIGS. 11A and 11B the arrays are linear. In other examples non-linear arrays may be used. In such examples the OLED pixels 103 and the OPV pixels 105 may be arranged in a non-linear arrangement such as spirals, concentric circles, curvilinear arrangements or any other suitable arrangement. In some examples the shapes of the OLED pixels 103 and the OPV pixels 105 may be arranged to maximise the area covered. For instances in the linear arrays of FIGS. 11A and 11B the OLED pixels 103 and the OPV pixels 105 are rectangular. In non-linear arrangements the OLED pixels 103 and the OPV pixels 105 may be circular, triangular, hexagonal, rhombic, rectangular or any other shape.

In some examples the all of the OLED pixels 103 within the display 101 may emit light at the same wavelength. For instance the OLED pixels 103 may be configured to emit green light to enable heart rate measurements to be obtained. In other examples the OLED pixels 103 within the display 101 may emit at different frequencies. For instance the display 101 may comprise some OLED pixels 103 which emit red light, some OLED pixels 103 which emit green light and some OLED pixels 103 which emit blue light. This may be achieved by using three different light emission compounds for red, green and blue, or in some configurations may be achieved by having a single white emitting OLED with a Red/Green/Blue (RGB) colour filter layer on top. In other examples some of the OLED pixels can be configured to emit infra red light which is able to penetrate more deeply into the user's tissue than the visible light.

Figure 12:
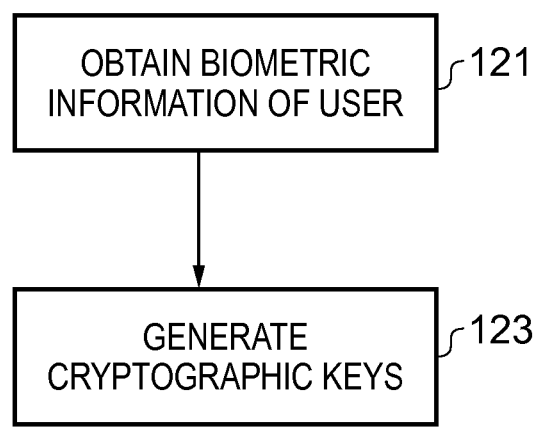
FIG. 12 illustrates a method of enabling identification of a user.

FIG. 12 illustrates a method of enabling identification of a user. The example method may be implemented using an apparatus 1 and electronic device 21 as described above. The electronic device 21 may comprise light sources 25 and photodetectors 27 as described above. Corresponding reference numerals are used to refer to corresponding features.

The method comprises, at block 121, obtaining biometric information of a user by detecting light scattered by biometric features of the user. The method also comprises, at block 123 generating cryptographic keys from the obtained biometric information wherein the cryptographic keys enable authentication of a user.

Figure 13:
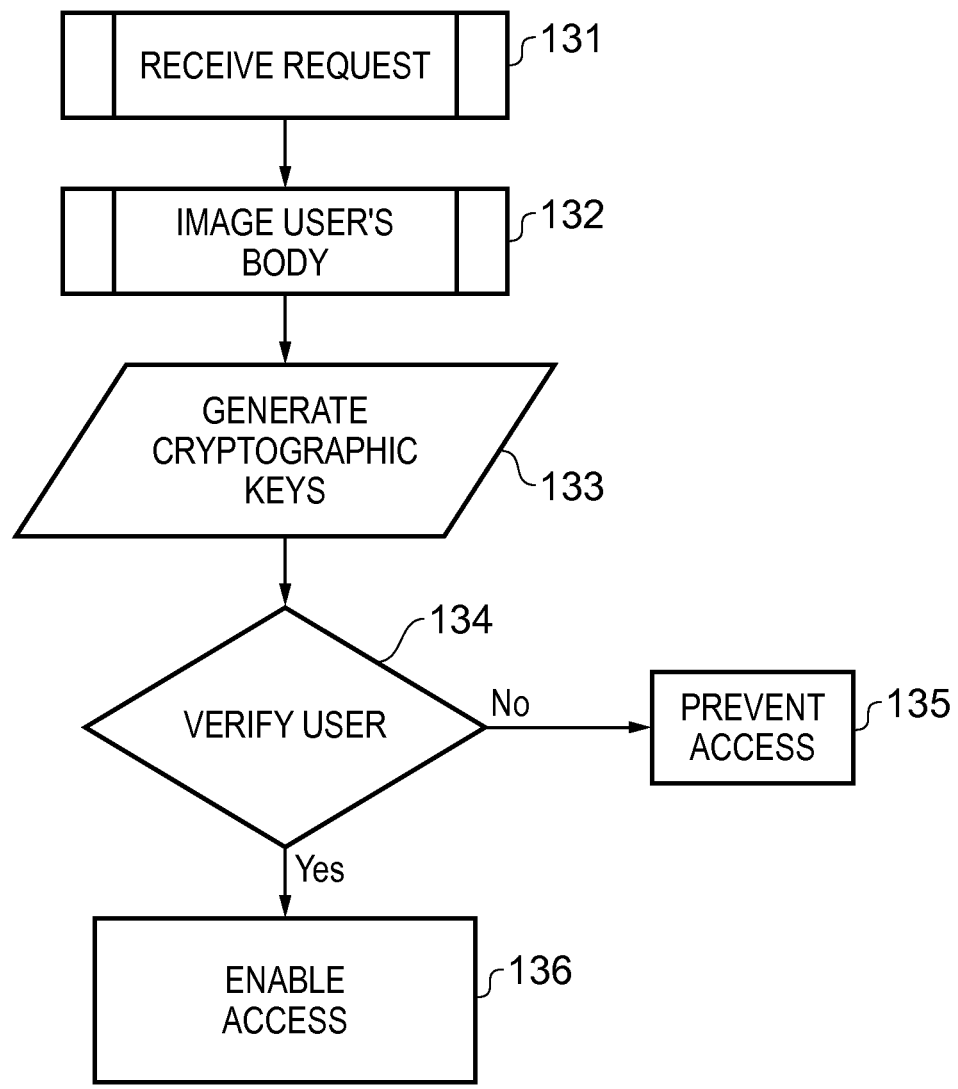
FIG. 13 illustrates another method of enabling identification of a user.

FIG. 13 illustrates another method of enabling identification of a user. The method may be implemented using the apparatus 1 and electronic devices 21 described above. Corresponding reference numerals are used for corresponding features.

The method of FIG. 13 comprises, at block 131, receiving a request for authentication of a user. The request may be received from a remote terminal. The remote terminal could be a personal device of the user such as a mobile phone or tablet computer. In such examples the user's personal devices may be requesting authentication of the user before enabling the user to access information or secure applications such as payment applications. In such examples the electronic device may be used to provide secure use of such devices.

The request may be received by the transceivers 29 of the electronic device 21. The request may be received using any suitable communication means such as low power wireless communication link. In some examples the link may comprise an NFC communication connection.

At block 132 the electronic device 21 images one or more portions of the user's body. The controlling circuitry 3 of the electronic device 21 may control the light source 25 and the photodetectors 27 to capture one or more images of the user's body.

The image which is captured may comprise biometric features of the user. The biometric features of the user may comprise any features which may enable the user to be uniquely identified. In some examples the biometric features may comprise the user's skin, patterns within the skin that may be unique to a user, the sub-cutaneous location of any blood vessels, the areas between the blood vessels, wrinkles in the skin, tendons and hair, light scattering or absorbing responses or any other suitable features.

In some examples of the disclosure the photodetectors 27 may be configured to detect single wavelengths or pluralities of different wavelengths. The photodetectors 27 may be configured to provide a two or three dimensional image of the sub-cutaneous structures of the user's body. The sub-cutaneous structures may comprise blood vessels, muscle tissue, tendons and bones or any other structures. The data obtained from the image may be used to generate a characteristic signal of the sub-cutaneous zone. The characteristic signal contains information unique to the user. The characteristic signal may comprise information which enables the user to be uniquely identified.

In some examples the characteristic signal may be loosely correlated to the blood vessel structure or other sub-cutaneous structures, so that the characteristic signal cannot be easily reconstructed. For instance, correlations in the characteristic signal may be removed so that the characteristic signal cannot be recreated from an approximate knowledge of typical blood vessels structures or other sub-cutaneous structures. In some examples the correlations may be removed by deriving the characteristic signal from the blood vessel structure or from areas between the blood vessels.

In some examples, the methods of FIGS. 3 and 4 may have already been performed. In such examples the light source 25 may be configured to selectively illuminate only the portions of the user's body which contain the relevant biometric features. In the example of FIG. 13 the relevant biometric features could be features which enable the user to be uniquely identified. In some examples this may comprise blood vessels, in other examples it may comprise patterns or other features in the skin of the user or any other suitable feature.

At block 133 the image data is used to generate cryptographic keys. In some examples the image data may be used to generate a public-private key pair which can be used for secure communications with the requesting device. As the image data is obtained from biometric features which are unique to the user the cryptographic keys which are obtained are also unique to the user.

In some examples the cryptographic keys may be generated from the characteristic signal which is obtained from the biometric features. The characteristic signal may be processed to increase the security of the cryptographic keys. In some examples correlations in the characteristic signal may be removed to increase the randomness of data which is used to generate the cryptographic keys. In some examples the characteristic signal may be scrambled to create a more secure key.

In some example information from different types of biometric features may be used to generate the cryptographic keys. For instance data obtained from blood vessels may be combined to data relating to the skin tone of the user or data relating to any other feature to generate a secure key. The data relating to the skin tone may comprise data relating to colour, roughness, wrinkliness, freckles, melanoma, or any other features. In other examples data obtained from blood vessels may be combined with data relating to additional information from measurements of heart rate, blood oxygenation, galvanic skin response, temperature or any other suitable feature. Using data from different features may provide more secure cryptographic keys. Using data from different features may reduce correlations within the data.

In some examples of the disclosure the electronic device 21 may be flexible. In such examples a strain sensor may be provided within the electronic device to measure the curvature of the electronic device 21 or a portion of the electronic device 21. This would ensure that different photodetector 27 geometries would be able to detect and recognise the characteristic signal from the biometric features of the user. In some examples the radius of curvature may also be combined with data obtained from blood vessels to generate the cryptographic key.

At block 134 the cryptographic keys are tested to verify the authenticity of the user. In some examples the public key may be tested. For instance, at block 134 a public key may be transmitted to the requesting device. In some examples the public key may be transmitted in an encrypted signal. In some examples the public key is only transmitted if it is confirmed that the requesting device is a trusted device. The key may be transmitted to the requesting terminal using a wireless connection or any other suitable means.

If at block 134 the user is not verified then the method moves to block 135 and the user is not authorised and access to secure functions is prevented.

If at block 134 the user is verified then the method moves to block 136 and the user is authorised and access to secure functions is enabled. Once the user is authorised this may enable the user to access functions such as private information and/or payment applications or any other suitable function. In some examples it may enable the user to be automatically associated with biometric parameters which are being monitored.

It is to be appreciated that the methods of FIGS. 12 and 13 may be used in any circumstances where a user needs to be authenticated. For instance it may be used to authorise payments or other wireless transactions, to enable access to secure facilities, homes, houses or hotel rooms to enable access to public transport systems, to identify the user associated with the obtained biometric parameters or any other circumstance.

In the examples of FIGS. 12 and 13 the cryptographic keys are generated by the electronic device 21 from obtained biometric data. By using the biometric data to generate the keys a unique cryptographic key may be generated. The use of the keys means that the biometric data used to generate the keys does not need to be transmitted between the wearable electronic device 21 and any other device. This may provide for a more secure system as the biometric data is never revealed but the electronic device 21 can confirm the existence or knowledge of the data.

Furthermore, the cryptographic key may be generated in response to the request from the other device. As the keys are generated from the biometric features of the user the key can be recreated at any point. The wearable electronic device may be configured to locate the biometric features and the selectively illuminate the correct portions of the user's skin to obtain the biometric data needed to recreate the key. This means that the information does not need to be stored in the wearable electronic device 21 as the key can be recreated when needed. This provides for a more secure system.

In the examples of FIGS. 12 and 13 the methods may be implemented by electronic devices 21 which are worn by the user. In other examples the methods may be implemented by devices which are not worn the user. For example sales terminals or secure entry systems may comprise devices which can implements such methods.

Examples of the disclosure provide many advantages. The wearable electronic device 21 may be efficient enough to be worn continuously. This may enable the wearable electronic device 21 to be used to continuously identify a user and/or continuously monitor biometric parameters of a user.

As the apparatus 1 is configured to enable selective illumination of the biometric features of the user this may provide for an efficient electronic device 21 with low power consumption. This may enable the electronic device 21 to be worn for long periods of time. This may make the examples of the disclosure suitable for monitoring the biometric parameters of user's for extended periods of time.

The apparatus 1 may be configured to change the the biometric features which are illuminated which may enable the same electronic device 21 to be used to monitor different parameters. For instance a pulse rate measurement may be obtained by illuminating a region which contains the fine network of arteriole and monitoring the change in absorbance due to change in blood volume in the illuminated region. A measurement of the blood oxygenation level of the blood flowing both towards and away from the heart may be obtained by illuminating a region which contains high volume blood carrying regions or selectively illuminating arteries or veins.

As the apparatus 1 is configured to enable selective illumination of the biometric features of the user this may enable accurate measurements of the biometric parameters to be obtained even if the electronic device 21 has moved on the users body. For example if the electronic device 21 is attached to a user's wrist the device 21 can detect that the relative positions of the user's biometric features to identify which portions should be illuminated. This may remove motion based errors from measurements obtained by the electronic device 21. In some examples the electronic device 21 may be configured to determine the amount and direction of any movement of the electronic device 21 relative to the skin of the user. In some examples the electronic device 21 may be configured to re-configure the selective illumination and/or detection to compensate for the movement.

The examples of the displays, light sources 25 and photodetectors 27 described above may enable a thin and lightweight electronic device 21 to be provided. This may enable the electronic device 21 to be worn continuously by a user without inconvenience or discomfort.

Examples of the disclosure may also enable the electronic device 21 to be used to authenticate a user. This may enable the user to be authorised without the need for RFID cards or other identification documents.

As the authentication of the user is based on the biometric parameters of the user it provides for a secure system because the biometric features are hard to copy. Furthermore the biometric features may only be detectable when the user's body is attached to the device. For instance the device can detect the presence of blood by detecting the amount of light absorbed by the oxygen in the blood. If an image or reproduction of the user's blood vessels was used instead this would not produce the same absorption effects and would not be recognised by the system.

In examples of the disclosure the electronic device 21 may be used to identify a user and monitor the location of the user. This may provide a plurality of useful applications. For instance, it enables military operations to be monitored remotely. The electronic device 21 can be used to determine, not just the location of military personnel but also their well being. Similarly, examples of the disclosure enable medical facilities such as hospitals and care homes to track the location of patients, nurses and other medical practitioners throughout their facilities. In some examples individuals may be tracked within their homes. This may be useful for monitoring the behaviour and wellbeing of elderly and/or infirm people. As the electronic device 21 is also used to monitor biometric parameters it may be used to monitor the well being of people entering hazardous environments such as soldiers, firemen, industrial plant workers or any other people.

The blocks illustrated in the FIGS. 3, 4 and 12 to 13 may represent steps in a method and/or sections of code in the computer program 9. The illustration of a particular order to the blocks does not necessarily imply that there is a required or preferred order for the blocks and the order and arrangement of the block may be varied. Furthermore, it may be possible for some blocks to be omitted.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed. For instance, in some examples the photodetectors 27 may be sensitive enough so that the biometric features can be detected just by using the infra red radiation emitted by the user's body. This may require a very sensitive photodetector 27 with a high dynamic range and/or a high gain amplifier.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method implemented by an apparatus, the method comprising:
   illuminating, by the apparatus, a portion of skin of a user;
   detecting, by the apparatus, light scattered by the illuminated portion of skin and using the detected light to identify locations of biometric features within the illuminated portion of skin; and
   configuring, by the apparatus, a light source to selectively illuminate identified locations of biometric features;
   wherein the light source is configured to illuminate the skin of the user and is also configured to illuminate a display.

2. A method as claimed in claim 1, wherein the biometric features comprise features which enable a user to be uniquely identified.

3. A method as claimed in claim 1, wherein the biometric features comprise blood vessels.

4. A method as claimed in claim 3, comprising identifying portions of regions illuminated by the light source overlying regions of high blood flow, and controlling the light source so that these regions are illuminated.

5. A method as claimed in claim 1 wherein the selective illumination of biometric features is used to identify a user.

6. A method as claimed in claim 5 wherein information obtained from the biometric features is used to create cryptographic key information which enables a user to be identified.

7. A method as claimed in claim 1 wherein the selective illumination of blood vessels is used to monitor biometric parameters of the user.

8. A method as claimed in claim 1 further comprising tuning an intensity of the illumination based on the intensity of the detected scattered light.

9. A method as claimed in claim 1 wherein a light source is configured to be provided adjacent to the skin of the user.

10. A method as claimed in claim 1 wherein the light source comprises a plurality of organic light emitting diodes.

11. A method as claimed in claim 1 wherein the scattered light is detected by a quantum dot detector.

12. A method as claimed in claim 1 wherein the areas of the user's skin which are selectively illuminated have a concentration of biometric features above a threshold.

13. An apparatus comprising:
processing circuitry; and
memory circuitry including computer program code;
the memory circuitry and the computer program code configured to, with the processing circuitry, cause the apparatus at least to perform;
illuminating a portion of skin of a user;
detecting light scattered by the illuminated portion of skin and using the detected light to identify locations of biometric features within the illuminated portion of skin; and
configuring a light source to selectively illuminate identified locations of biometric features;
wherein the light source is configured to illuminate the skin of the user and is also configured to illuminate a display.

14. A apparatus as claimed in claim 13, wherein the biometric features comprise blood vessels.

15. A an apparatus as claimed in claim 13 wherein the light source comprises a plurality of organic light emitting diodes.

16. An apparatus as claimed in claim 13 comprising a quantum dot detector configured to detect the scattered light.

17. A non-transitory computer readable medium comprising a computer program comprising computer program instructions that, when executed by processing circuitry, enable controlling an apparatus to:
illuminate a portion of skin of a user;
detect light scattered by the illuminated portion of skin and using the detected light to identify locations of biometric features within the illuminated portion of skin; and
configure a light source to selectively illuminate identified locations of biometric features;
wherein the light source is configured to illuminate the skin of the user and is also configured to illuminate a display.

18. A non-transitory computer readable medium as claimed in claim 17, wherein the biometric features comprise features which enable a user to be uniquely identified.

* * * * *